United States Patent [19]
Mizutani et al.

[11] Patent Number: 6,072,089
[45] Date of Patent: *Jun. 6, 2000

[54] PROCESS FOR PRODUCING 1,5-PENTANEDIOL DERIVATIVES

[75] Inventors: Satoru Mizutani, Yokkaichi; Toshiaki Ogata, Ichihara; Nobuhito Amemiya; Kenji Mutoh, both of Yokkaichi, all of Japan

[73] Assignee: Kyowa Yuka Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/903,066

[22] Filed: Jul. 30, 1997

Related U.S. Application Data

[63] Continuation-in-part of application No. PCT/JP95/02441, Nov. 30, 1995.

[51] Int. Cl.[7] .................................................. C07C 27/04
[52] U.S. Cl. ............................................. 568/862; 549/423
[58] Field of Search .................................. 568/852, 853, 568/861, 865, 862

[56] References Cited

U.S. PATENT DOCUMENTS 2,317,456  4/1943  Handford ................................. 260/602
3,046,311  7/1962  Milligan .

FOREIGN PATENT DOCUMENTS 2410156    9/1975   Germany .
53-101308  9/1978   Japan .
54-27510   3/1979   Japan .
482970     4/1938   United Kingdom ................... 568/862

OTHER PUBLICATIONS

F. Weiss, A. Isard, vol. 197. pp. 1355–1364.
Bulletin de la Societe Chimique de France, 1965, 1355.
Tetrahedron, 18 657 (1962).
Chemical Abstract,84,43291x (1976).
The Journal of American Chemical Society, 95, 6757 (1973).
The Journal of American Chemical Society, 77, 1862 (1955).
Journal of Organic Chemistry, 48, 5170 ( 1983).
Tetrahedon, 18 657 (1962).
STN, file :Merck, citation No. 7256, 1,5–pentanediol.

*Primary Examiner*—Michael L. Shippen
*Attorney, Agent, or Firm*—Antonelli, Terry, Stout, & Kraus, LLP

[57] ABSTRACT

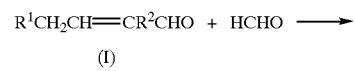

(I)

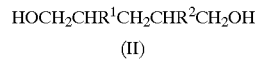

(II)

(In the formulae, $R^1$ and $R^2$, which may be the same or different, each represents hydrogen or lower alkyl.)

The present invention relates to a process for producing 1,5-pentanediol derivatives represented by general formula (II) which comprises reacting 2-butenal derivatives represented by general formula (I) with formaldehyde, and hydrogenating the obtained mixture of reaction products.

10 Claims, No Drawings

PROCESS FOR PRODUCING 1,5-PENTANEDIOL DERIVATIVES

This application is a continuation-in-part of International Application No. PCT/JP95/02441, filed Nov. 30, 1995.

TECHNICAL FIELD

The present invention relates to a process for producing 1,5-pentanediol derivatives, and to 5,6-dihydro-2H-2-pyranol derivatives which are useful as intermediates for the synthesis of 1,5-pentanediol derivatives.

1,5-Pentanediol derivatives are useful as materials for polyesters, polyester polyols, alkyds, polyurethanes, and reactive monomers, which are used in preparing coatings, adhesives, inks, fibers, films, synthetic leathers, plasticizers, lubricating oils, elastomers, foams, and molding materials. They are also useful as materials for organic synthesis and as wetting agents.

BACKGROUND ART

As a method for producing 2- and/or 4-substituted or unsubstituted 1,5-pentanediol derivatives from 2-butenal derivatives, Method (A) is known, in which 2-butenal derivatives are subjected to a reaction with formaldehyde, and the formed intermediates (5-hydroxy-2-pentenal derivatives) are separated from the reaction mixture and then subjected to catalytic reduction [U.S. Pat. No. 3,046,311 (1962)]. However, according to the Examples of said patent, the yield of the intermediate (5-hydroxy-2,4-dimethyl-2-pentenal) based on the consumed 2-methyl-2-pentenal is as low as 63%, and the yield of 5-hydroxy-2-pentenal from crotonaldehyde is only 12%.

Some methods are known for the production of 2,4-dimethyl-1,5-pentanediol; for example, Method (B) in which diethyl methylmalonate and methyl methacrylate, as starting materials, are subjected to a three step reaction and then reduced with lithium aluminum hydride [The Journal of American Chemical Society, 77, 1862 (1955); Chemical Abstracts, 50, 2583d (1956)], Method (C) in which 2-methyl-4-methyleneglutaraldehyde obtained by pyrolyzing 2-ethenyl-5-methylene-1,3-dioxane is subjected to catalytic reduction with Raneynickel as acatalyst [Bulletinde la Societe Chimique de France, 1965, 1355; Chemical Abstracts, 63, 11546e (1965)], and Method (D) in which 2,4-dimethyl-1,4-pentadiene is subjected to hydroboration [The Journal of American Chemical Society, 95, 6757 (1973); Chemical Abstracts, 80, 3372k (1974)]. However, Methods (B) and (D) are unsuitable for industrial application, because expensive reagents such as lithium aluminum hydride and borane are required in the processes. In Method (C), the desired product is obtained only at a low yield.

As a method for producing 2,4-diethyl-1,5-pentanediol, Method (E) is known, in which 3,5-diethyl tetrahydropyran formed by hydroformylation of 2-ethyl-2-hexenol is subjected to catalytic reduction [German Patent No. 2,410,156 (1975); Chemical Abstracts, 84, 43291x (1976)]. However, 2,4-diethyl-1,5-pentanediol is a by-product obtained in the synthesis of 2-ethyl-3-propyl-1,4-butanediol and its yield is extremely low.

As for the production of 5,6-dihydro-2H-2-pyranol, some methods have been reported; for example, Method (F) in which 3-bromotetrahydro-2-pyranol is subjected to a reaction in alcohol in the presence of sodium [Tetrahedron, 18, 657 (1962); Chemical Abstracts, 57, 11150c (1962)], Method (G) in which 5,6-dihydro-2-pyrone is reduced with diisobutylaluminum hydride [Journal of Organic Chemistry, 48, 5170 (1983)], and Method (H) in which 2-hydroperoxy-5,6-dihydro-2H-pyrane is subjected to a catalytic reduction (Japanese Published Unexamined Patent Application No. 101308/78). However, industrial production of 3- and/or 5-alkyl-substituted-5,6-dihydro-2H-2-pyranol derivatives according to the above Methods (F)-(H) is difficult, because raw materials for the synthesis are not readily available. 4-Alkyl-substituted-5,6-dihydro-2H-2-pyranol is described in Japanese Published Unexamined Patent Application No. 101308/78.

DISCLOSURE OF THE INVENTION

The present inventors have found that a reaction of a 2-butenal derivative represented by general formula (I):

$$R^1CH_2CH=CR^2CHO \qquad (I)$$

(wherein $R^1$ and $R^2$, which may be the same or different, each represents hydrogen or lower alkyl) [hereinafter referred to as Compound (I), and the same applies to the compounds of other formula numbers] with formaldehyde affords a 5,6-dihydro-2H-2-pyranol derivative of an unsaturated hemiacetal structure represented by general formula (III):

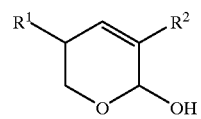

(III)

(wherein $R^1$ and $R^2$ have the same significances as defined above) besides a 5-hydroxy-2-pentenal derivative [corresponding to the compound represented by general formula (IV) shown below], and that the hydrogenation reaction of Compound (III) affords a 1,5-pentanediol derivative represented by general formula (II):

$$HOCH_2CHR^1CH_2CHR^2CH_2OH \qquad (II)$$

(wherein $R^1$ and $R^2$ have the same significances as defined above). They have also found that Compound (II) can be efficiently produced by the hydrogenation reaction of a mixture of the above Compound (III) formed by the reaction of Compound (I) with formaldehyde and a 5-hydroxy-2-pentenal derivative represented by general formula (IV):

$$HOCH_2CHR^1CH=CR^2CHO \qquad (IV)$$

(wherein $R^1$ and $R^2$ have the same significances as defined above).

The present invention relates to a process for producing Compound (II) which comprises subjecting Compound (I) to a reaction with formaldehyde and then hydrogenating the obtained mixture of reaction products, and to a process for producing Compound (II) which comprises hydrogenating Compound (III).

The present invention also provides 5,6-dihydro-2H-2-pyranol derivatives represented by general formula (IIIa):

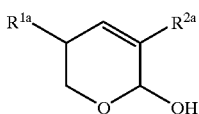

(wherein $R^{1a}$ and $R^{2a}$, which may be the same or different, each represents hydrogen or lower alkyl, provided at least one of $R^{1a}$ and $R^{2a}$ represents lower alkyl).

In the definitions of the groups in general formulae (I) to (IV), the lower alkyl means a straight-chain or branched alkyl group having 1 to 6 carbon atoms, such as methyl, ethyl, propyl, isopropyl, butyl, isobutyl, sec-butyl, tert-butyl, pentyl, neopentyl, and hexyl.

The present invention is described in detail below.

Process 1

Compound (II) can be prepared according to the following reaction steps.

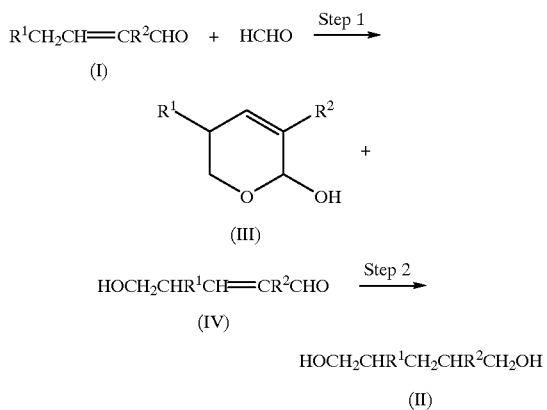

(In the formulae, $R^1$ and $R^2$ have the same significance as defined above.)

Step 1

A mixture of Compounds (III) and (IV) can be obtained by subjecting Compound (I) to a reaction with formaldehyde by the use of a basic catalyst in the presence or absence of a water-soluble organic solvent.

Examples of Compound (I) are crotonaldehyde (2-butenal), 2-pentenal, 2-methyl-2-butenal, 2-hexenal, 2-methyl-2-pentenal, 2-ethyl-2-butenal, 2-heptenal, 2-methyl-2-hexenal, 2-ethyl-2-pentenal, 2-propyl-2-butenal, 2-methyl-2-heptenal, 2-ethyl-2-hexenal, 2-propyl-2-pentenal, 2-ethyl-2-heptenal, 2-propyl-2-hexenal, 2-propyl-2-heptenal, 5-methyl-2-hexenal, 2-isopropyl-2-butenal, 2,5-dimethyl-2-hexenal, 2-isopropyl-2-pentenal, 2-ethyl-5-methyl-2-hexenal, 2-isopropyl-2-hexenal, 2-isopropyl-5-methyl-2-hexenal, 5-methyl-2-propyl-2-hexenal, 2-isopropyl-2 -heptenal, 2-octenal, 2-nonenal, and 2-decenal. Preferred are crotonaldehyde, 2-methyl-2-pentenal, 2-ethyl-2-hexenal, and 2-ethyl-2-butenal.

These 2-butenal derivatives can be easily prepared by aldol condensation and dehydration, which are known methods, using as raw materials one or two kinds of aldehydes selected from acetaldehyde, propionaldehyde, butyraldehyde, valeraldehyde, isovaleraldehyde, hexylaldehyde, heptylaldehyde, and octylaldehyde.

As the formaldehyde, a 30–50 wt % aqueous solution which is commercially available (formalin) or 70–95 wt % paraformaldehyde can be used. Preferably, formalin is used. The molar ratio of formaldehyde to Compound (I) is 0.4–2:1, preferably 0.5–1.5:1.

Suitable basic catalysts include alkali metal hydroxides such as lithium hydroxide, sodium hydroxide, and potassium hydroxide, alkaline earth metal hydroxides such as calcium hydroxide and magnesium hydroxide, alkali metal carbonates such as sodium carbonate and potassium carbonate, sodium alcoholates such as sodium methylate, sodium ethylate, and sodium butylate, tertiary amines such as triethylamine and tributylamine, quaternary ammonium hydroxides such as benzyltrimethylammonium hydroxide and tetrabutylammonium hydroxide, and strongly basic ion-exchange resins. Of these catalysts, alkali metal hydroxides and alkali metal carbonates are economically preferred. Particularly preferred are sodium hydroxide, potassium hydroxide, and potassium carbonate. The molar ratio of the catalyst to Compound (I) is 0.01–0.5:1, preferably 0.02–0.3:1. The above basic catalysts may be used as aqueous solutions.

Compound (I) and the compounds formed are substantially water-insoluble. When formalin is used as formaldehyde, the reaction mixture is heterogeneous and separated into two layers within the above molar ratio range, and so it is preferred to add a water-soluble organic solvent. Any water-soluble organic solvent can be used as long as it is inert under the reaction conditions. Preferred solvents are alcohols such as methanol, ethanol, propanol, isopropyl alcohol, ethylene glycol, and propylene glycol, ethers such as dimethoxyethane, tetrahydrofuran, and dioxane, and glycol ethers such as ethylene glycol monoethyl ether. The amount of the organic solvent used is not limited, but is preferably 100 wt % or below based on the total amount of Compound (I) and formalin.

The reaction temperature is 15–100° C., preferably 30–80° C., though it varies with the kind and amount of the catalyst. The reaction time is usually 1–10 hours, though it varies with the reaction temperature, and the kind and amount of the catalyst.

After the reaction is completed, a mixture of Compounds (III) and (IV) can be purified according to purification methods usually used in synthetic organic chemistry, such as filtration, extraction, washing, drying, concentration, distillation, and various kinds of chromatography. The reaction mixture can be subjected to the subsequent hydrogenation reaction as such, but it is preferably subjected to post-treatment according to ordinary methods such as neutralization, concentration, separation, and washing with water for removal of impurities to obtain a mixture mainly comprising Compounds (III) and (IV). For example, the reaction mixture is concentrated under reduced pressure to distill the organic solvent, and the resulting mixture is separated into an organic layer and a water layer. Then, the organic layer containing the desired intermediates is washed with water. The separation of the mixture into two layers may be effected even without concentration depending upon the amount of the organic solvent used in the reaction, but it is usually preferable to remove the used organic solvent. Neutralization of the reaction mixture is not necessarily required. Any neutralizing agent can be used, and preferably, mineral acids such as sulfuric acid and hydrochloric acid are used. The amount of water used for washing and the number of times of washing are not specifically limited, but it is preferred to carry out washing one to five times using 0.2–1.5 times as much water as the organic layer. The washing temperature is usually 10–90° C., preferably 20–70° C., and the washing time is 5–60 minutes per washing, preferably 10–30 minutes.

Step 2

Compound (II) can be obtained by hydrogenating the mixture of Compounds (III) and (IV) obtained in Step 1.

The hydrogenation reaction of the mixture of Compounds (III) and (IV) to form Compound (II) is carried out by dispersing or suspending a hydrogenation catalyst in the mixture of Compounds (III) and (IV) in an appropriate solvent or without a solvent in the presence of hydrogen, or by supplying a solution of the mixture of Compounds (III) and (IV) to a reaction tube packed with said catalyst.

Any solvent may be used in the above reaction as long as it is inert under the reaction conditions. Suitable solvents include alcohols such as methanol, ethanol, propanol, isopropyl alcohol, and butanol, ethers such as dimethoxyethane, tetrahydrofuran, and dioxane, water, and mixtures thereof. Suitable hydrogenation catalysts are those containing, as active components, one or more metals such as nickel, ruthenium, platinum, copper, and rhodium. Also catalysts which further contain metals such as chrome, zinc, barium, aluminum, magnesium, and tungsten in addition to the above metals are preferably used.

Generally, the hydrogenation reaction is carried out at 30–200° C., preferably 50–150° C., at a hydrogen pressure of 1–150 kg/cm$^2$, preferably 5–80 kg/cm$^2$, in a stirring autoclave or a reaction tube, by either batch method or continuous method.

After the reaction is completed, Compound (II) can be isolated and purified from the reaction mixture according to ordinary methods. For example, the desired compound can be purified by removing the catalyst from the reaction mixture, distilling compounds with low boiling points from the mixture at atmospheric pressure or under reduced pressure, and then distilling the obtained residue under reduced pressure.

Examples of Compound (II) are 1,5-pentanediol, 2-methyl-1,5-pentanediol, 2-ethyl-1,5-pentanediol, 2,4-dimethyl-1,5-pentanediol, 2-propyl-1,5-pentanediol, 2-ethyl-4-methyl-1,5-pentanediol, 2-methyl-4-propyl-1,5-pentanediol, 2,4-diethyl-1,5-pentanediol, 2-ethyl-4-propyl-1,5-pentanediol, 2,4-dipropyl-1,5-pentanediol, 2-isopropyl-1,5-pentanediol, 2-isopropyl-4-methyl-1,5-pentanediol, 2-ethyl-4-isopropyl-1,5-pentanediol, 2,4-diisopropyl-1,5-pentanediol, 2-isopropyl-4-propyl-1,5-pentanediol, 2-butyl-1,5-pentanediol, 2-pentyl-1,5-pentanediol, and 2-hexyl-1,5-pentanediol. Preferred are 1,5-pentanediol, 2,4-dimethyl-1,5-pentanediol, 2,4-diethyl-1,5-pentanediol, and 2-ethyl-1,5-pentanediol.

Process 2

Compound (IIIa) can be prepared from Compound (Ia), i.e., Compound (I) wherein at least one of R$^1$ and R$^2$ is not hydrogen, according to the same method as in Step 1 of Process 1.

Isolation of the desired Compound (IIIa) from the reaction mixture is carried out according to ordinary methods such as neutralization, concentration, separation, washing with water, and distillation. For example, the reaction mixture is concentrated under reduced pressure to distill the organic solvent, and the resulting mixture is separated into an organic layer and a water layer. Then, the organic layer containing the desired compound is washed with water, followed by distillation. The separation of the mixture into two layers may be effected even without concentration depending upon the amount of the organic solvent used in the reaction, but it is usually preferable to remove the used organic solvent. Neutralization of the reaction mixture is not necessarily required. Any neutralizing agent can be used, and preferably, mineral acids such as sulfuric acid and hydrochloric acid are used. The amount of water used for washing and the number of times of washing are not specifically limited, but it is preferred to carry out washing one to five times using 0.2–1.5 times as much water as the organic layer. The washing temperature is usually 10–90° C., preferably 20–70° C., and the washing time is 5–60 minutes per washing, preferably 10–30 minutes. Distillation is carried out at atmospheric pressure or under reduced pressure.

Examples of Compound (IIIa) are 3-methyl-5,6-dihydro-2H-2-pyranol, 5-methyl-5,6-dihydro-2H-2-pyranol, 3-ethyl-5,6-dihydro-2H-2-pyranol, 5-ethyl-5,6-dihydro-2H-2-pyranol, 3,5-dimethyl-5,6-dihydro-2H-2-pyranol, 3-propyl-5,6-dihydro-2H-2-pyranol, 5-propyl-5,6-dihydro-2H-2-pyranol, 3-ethyl-5-methyl-5,6-dihydro-2H-2-pyranol, 5-ethyl-3-methyl-5,6-dihydro-2H-2-pyranol, 3-methyl-5-propyl-5,6-dihydro-2H-2-pyranol, 5-methyl-3-propyl-5,6-dihydro-2H-2-pyranol, 3,5-diethyl-5,6-dihydro-2H-2-pyranol, 3-ethyl-5-propyl-5,6-dihydro-2H-2-pyranol, 5-ethyl-3-propyl-5,6-dihydro-2H-2-pyranol, 3,5-dipropyl-5,6-dihydro-2H-2-pyranol, 3-isopropyl-5,6-dihydro-2H-2-pyranol, 5-isopropyl-5,6-dihydro-2H-2-pyranol, 3-isopropyl-5-methyl-5,6-dihydro-2H-2-pyranol, 5-isopropyl-3-methyl-5,6-dihydro-2H-2-pyranol, 3-ethyl-5-isopropyl-5,6-dihydro-2H-2-pyranol, 5-ethyl-3-isopropyl-5,6-dihydro-2H-2-pyranol, 3,5-diisopropyl-5,6-dihydro-2H-2-pyranol, 3-isopropyl-5-propyl-5,6-dihydro-2H-2-pyranol, 5-isopropyl-3-propyl-5,6-dihydro-2H-2-pyranol, 5-butyl-5,6-dihydro-2H-2-pyranol, 5-pentyl-5,6-dihydro-2H-2-pyranol, and 5-hexyl-5,6-dihydro-2H-2-pyranol. Preferred are 3,5-dimethyl-5,6-dihydro-2H-2-pyranol, 3,5-diethyl-5,6-dihydro-2H-2-pyranol, and 3-ethyl-5,6-dihydro-2H-2-pyranol.

Process 3

Compound (II) can also be prepared from Compound (III) according to the same method as in Step 2 of Process 1.

Certain embodiments of the invention are illustrated in the following Examples.

BEST MODE FOR CARRYING OUT THE INVENTION

EXAMPLE 1

To a mixture of 726g of 2-ethyl-2-hexenal (purity: 99.0%, 5.7 mol), 308 g (3.8 mol) of 37% formalin, and 517 g of methanol heated to 50° C. was added dropwise with stirring 60.8 g (0.38 mol) of a 25% aqueous solution of sodium hydroxide over one hour. After the dropping was completed, the mixture was further stirred at 50° C. for 3 hours. The reaction mixture was analyzed by gas chromatography (the internal standard method with diethylene glycol dimethyl ether as an internal standard), and the yields of 2,4-diethyl-5-hydroxy-2-pentenal and 3,5-diethyl-5,6-dihydro-2H-2-pyranol based on the used formaldehyde and the consumed 2-ethyl-2-hexenal were found to be as follows.

|  | Yield (%) | |
| --- | --- | --- |
|  | Based on aldehyde | Based on 2-ethyl-2-hexenal |
| 2,4-diethyl-5-hydroxy-2-pentenal | 58 | 66 |
| 3,5-diethyl-5,6-dihydro-2H-2-pyranol | 26 | 30 |
| Total | 84 | 96 |

After methanol was distilled off from the reaction mixture under reduced pressure (100–50 mmHg, bath temperature: 65° C.), 430 ml of water was added to the residue. After stirring at 55° C. for 10 minutes, the mixture was allowed to stand for about 20 minutes, and then the water layer was removed. This washing treatment with water was repeated twice more to obtain an organic layer (769 g). Then, 675 g of the obtained organic layer was put into a 1000-ml autoclave together with 34 g of a nickel catalyst (N. E. Chemcat; Harshaw-Ni5258E), and the mixture was heated at 120° C. with stirring for 4 hours. During the reaction, the hydrogen pressure was kept at 25 kg/cm². After the reaction was completed, the reaction mixture was analyzed by gas chromatography, and the yield of 2,4-diethyl-1,5-pentanediol formed by the hydrogenation reaction was found to be 91%.

After the catalyst was filtered off from the reaction mixture, the fraction distilled at 133–137° C. under reduced pressure (2 mmHg) was recovered to give 375 g of 2,4-diethyl-1,5-pentanediol. The overall yield of 2,4-diethyl-1,5-pentanediol was 70% based on the formaldehyde, and 80% based on the consumed 2-ethyl-2-hexenal.

The structure of the product was confirmed by mass spectrum and $^1$H-NMR.

Mass spectrum (CI method, m/z): 161 (weak, M+1) 143 (strong, M-H$_2$O+1)

Mass spectrum (EI method, m/z): 161 (M+1)

$^1$H-NMR (CDCl$_3$, δ): 0.91(6H, t, J=7.4Hz), 1.1–1.6(8H, m), 2.66(1H, br, —OH), 3.03(1H, br, —OH), 3.42–3.66 (4H, m)

$^1$H-NMR (CDCl$_3$+D$_2$O, δ): 0.90(6H, t, J=7.4 Hz), 1.1–1.6 (8H, m), 3.43(1H, dd, J=5.6, 10.7 Hz), 3.49(1H, dd, J=6.4, 10.5 Hz), 3.55(1H, dd, J=5.3, 10.5 Hz), 3.62(1H, dd, J=3.9, 10.7 Hz)

EXAMPLE 2

To a mixture of 28.7 g of 2-ethyl-2-hexenal (purity: 99.0%, 0.225 mol), 12.5 g (0.15 mol) of 37% formalin, and 25 ml of methanol heated to 50° C. was added dropwise 3.37 g (0.015 mol) of a 25% aqueous solution of potassium hydroxide over 20 minutes. After the dropping was completed, the mixture was further stirred at 50° C. for 4 hours. The reaction mixture was analyzed by gas chromatography (the internal standard method with diethylene glycol dimethyl ether as an internal standard), and the yields of 2,4-diethyl-5-hydroxy-2-pentenal and 3,5-diethyl-5,6-dihydro-2H-2-pyranol based on the used formaldehyde and the consumed 2-ethyl-2-hexenal were found to be as follows.

|  | Yield (%) | |
| --- | --- | --- |
|  | Based on aldehyde | Based on 2-ethyl-2-hexenal |
| 2,4-diethyl-5-hydroxy-2-pentenal | 60 | 63 |
| 3,5-diethyl-5,6-dihydro-2H-2-pyranol | 33 | 34 |
| Total | 93 | 97 |

After methanol was distilled off from the reaction mixture under reduced pressure (100–50 mmHg, bath temperature: 65° C.), 18 ml of water was added to the residue. After stirring at 55° C. for 10 minutes, the mixture was allowed to stand for about 20 minutes, and the water layer was removed. This washing treatment with water was repeated twice more, and the organic layer was put into a 100-ml autoclave together with 1.5 g of Raney nickel, 25 ml of methanol, and 5 ml of water, followed by stirring at 120° C. for 4 hours at a hydrogen pressure of 25 kg/cm². After the reaction was completed, the reaction mixture was analyzed by gas chromatography, and the yield of 2,4-diethyl-1,5-pentanediol formed by the hydrogenation reaction was found to be 92%.

EXAMPLE 3

To a mixture of 776 g of 2-ethyl-2-hexenal (purity: 97.6%, 6.0 mol), 324 g (4.0 mol) of 37% formalin, and 550 g of methanol heated to 50° C. was added dropwise with stirring 64 g (0.4 mol) of a 25% aqueous solution of sodium hydroxide over one hour. After the dropping was completed, the mixture was further stirred at 50° C. for 3 hours. The reaction mixture was analyzed by gas chromatography (the internal standard method with diethylene glycol dimethyl ether as an internal standard), and the yields of 3,5-diethyl-5,6-dihydro-2H-2-pyranol based on the used formaldehyde and the consumed 2-ethyl-2-hexenal were found to be 26% and 30%, respectively.

After methanol was distilled off from the reaction mixture under reduced pressure (100–50 mmHg, bath temperature: 60° C.), 550 ml of water was added to the residue. After stirring at 55–60° C. for 10 minutes, the mixture was allowed to stand for about 10 minutes, and the water layer was removed. This washing treatment with water was repeated twice more, and the organic layer was rectified using a McMahon packed column (inside diameter: 50 mm, height: 1 m). The fraction distilled at 97–98° C./1 mmHg was recovered to give 89.1 g of 3,5-diethyl-5,6-dihydro-2H-2-pyranol (purity: 99%), and the fraction distilled at 110° C./1 mmHg was recovered to give 99.5 g of 2,4-diethyl-5-hydroxy-2-pentenal (purity: 95%).

The structures of the products were confirmed by mass spectrum and $^1$H-NMR. The $^1$H-NMR data revealed that 3,5

-diethyl-5,6-dihydro-2H-2-pyranol is a mixture of cis-trans isomers (ca. 3:2).

3,5-diethyl-5,6-dihydro-2H-2-pyranol

Mass spectrum (CI method, m/z): 157 (weak, M+1), 139 (strong, M—H$_2$O+1)

Mass spectrum (EI method, m/z): 139 (M—OH)

$^1$H-NMR (CDCl$_3$, δ): 0.95(3H, t, J7.4 Hz), 1.06(3H, t, J=7.4 Hz), 1.25–1.35 and 1.35–1.5 (2H, 3:2, m), 1.85 and 2.22(1H, 2:3, 2 bs), 2.0–2.2(2H, m), 2.88 and 2.89 (1H, 2 d, J=5.6 and 5.4 Hz), 3.57 and 3.57(1H, t and dt, t:J=10.7 Hz, dt:J=1.6, 11.3 Hz), 3.74 and 4.05(1H, 3:2, ddd and dd, ddd:J=1.2, 5.6, 10.7 Hz, dd: J=4.0, 11.3 Hz), 5.16 and 5.02 (1H, 2:3, 2d, J=5.1 and 4.9 Hz), 5.56 and 5.66(1H, 3:2, s and d, d:J=4.9 Hz)

2,4-diethyl-5-hydroxy-2-pentenal

Mass spectrum (CI method, m/z): 157 (M+1)

Mass spectrum (EI method, m/z): 126 (M—HCHO)

$^1$H-NMR (CDCl$_3$, δ): 0.92(3H, t, J=7.5 Hz), 1.00(3H, t, J=7.6 Hz), 1.3–1.45(1H, m), 1.6–1.75(1H, m), 2.25–2.4(2H, m), 2.7–2.85(1H, m), 3.05(1H, br), 3.61(1H, dd, J=7.1, 10.7 Hz), 3.70(1H, dd, J=5.4, 10.7 Hz), 6.25(1H, d, J=10.5 Hz), 9.39(1H, s)

EXAMPLE 4

3,5-Diethyl-5,6-dihydro-2H-2-pyranol obtained in Example 3 (5 g) was put into a 100-ml autoclave together with 0.25 g of Raney nickel and 0.5 ml of water, followed by stirring at 120° C. for 5 hours at a hydrogen pressure of 30 kg/cm$^2$. After the catalyst was filtered off from the reaction mixture, water was distilled under reduced pressure to obtain 2,4-diethyl-1,5-pentanediol quantitatively.

Industrial Applicability

The present invention provides a process for producing 1,5-pentanediol derivatives, and 5,6-dihydro-2H-2-pyranol derivatives which are useful as intermediates for the sysnthesis of 1,5-pentanediol derivatives.

What is claimed is:

1. A process for producing a 1,5-pentanediol derivative represented by general formula (II):

HOCH$_2$CHR$^1$CH$_2$CHR$^2$CH$_2$OH            (II)

(wherein R$^1$ and R$^2$, which may be the same or different, and each represents a lower alkyl) which comprises reacting a 2-butenal derivative represented by general formula (I):

R$^1$CH$_2$CH=CR$^2$CHO            (I)

(wherein R$^1$ and R$^2$ have the same significance as defined above) with formaldehyde, and then hydrogenating the obtained mixture of reaction products without separating a 5-hydroxy-2-pentenal derivative from the obtained mixture, to obtain a 1.5-pentanediol derivative.

2. The process of claim 1, wherein 1,5-pentanediol is the main product of the process.

3. The process of claim 1, wherein a reaction temperature of the process is 15–100° C.

4. The process of claim 1, wherein the yield of a 1,5-pentanediol derivative based on a 2-butene-1-al derivative consumed is 80%.

5. The process of claim 1, wherein the yields of 2,4-diethyl-5-hydroxy-2-pentenal and 3,5-diethyl-5,6-dihydro-2H -pyranol based on formaldehyde used and the consumed 2-ethyl-2-hexenal are 84% and 96%, respectively.

6. The process of claim 1, wherein the yield of 2,4-diethyl-1,5-pentanediol formed by hydrogenation reaction is 91%.

7. A process for producing a 1,5-pentanediol derivative represented by general formula (II):

HOCH$_2$CHR$^1$CH$_2$CHR$^2$CH$_2$OH            (II)

(wherein R$^1$ and R$^2$, which may be the same or different, and each represents a lower alkyl) which consists essentially of reacting a 2-butenal derivative represented by general formula (I):

R$^1$CH$_2$CH=CR$^2$CHO            (I)

(wherein R$^1$ and R$^2$ have the same significance as defined above) with formaldehyde, and then hydrogenating the obtained mixture of reaction products to obtain a 1,5-pentanediol derivative.

8. The process of claim 7, wherein 1,5-pentanediol is the main product of the process.

9. A process for producing a 1,5-pentanediol derivative represented by general formula (II):

HOCH$_2$CHR$^1$CH$_2$CHR$^2$CH$_2$OH            (II)

(wherein R$^1$ and R$^2$, which may be the same or different, and each represents a lower alkyl) which consists of reacting a 2-butenal derivative represented by general formula (I):

R$^1$CH$_2$CH=CR$^2$CHO            (I)

(wherein R$^1$ and R$^2$ have the same significance as defined above) with formaldehyde, and then hydrogenating the obtained mixture of reaction products, to obtain a 1,5-pentanediol derivative.

10. The process of claim 9, wherein 1,5-pentanediol is the main product of the process.

* * * * *